United States Patent [19]

Yamashita et al.

[11] Patent Number: 4,696,895

[45] Date of Patent: Sep. 29, 1987

[54] MONOCLONAL ANTI-PROTEIN C ANTIBODY, ITS PREPARATION AND USE THEREOF

[75] Inventors: Tatsuo Yamashita, Kobe; Masafumi Terada, Higashiosaka; Koji Suzuki, Tsu, all of Japan

[73] Assignee: Fujisawa Pharmaceutical Co., Ltd., Osaka, Japan

[21] Appl. No.: 658,560

[22] Filed: Oct. 9, 1984

[30] Foreign Application Priority Data

Oct. 18, 1983 [GB] United Kingdom ............... 8327860

[51] Int. Cl.[4] ................ G01N 33/53; G01N 33/535; G01N 33/577
[52] U.S. Cl. .................................. 435/7; 435/68; 435/172.2; 435/948; 435/240.27; 436/548; 436/815; 530/387; 530/808; 935/103; 935/110
[58] Field of Search ............... 435/7, 172.2, 810, 240, 435/13, 68; 436/548, 811, 815; 935/89, 95, 103, 110; 260/112 B, 112 R; 530/387, 808

[56] References Cited

U.S. PATENT DOCUMENTS 4,486,530 12/1984 David et al. ..................... 435/7

OTHER PUBLICATIONS

Chemical Abstracts, I, 100: 170454b (1984).
Chemical Abstracts, II, 101: 166500s (1984).
Chemical Abstracts, III, 103: 209427j (1985).
Arvin et al. "Infection and Immunity," vol. 40, No. 1 (Apr. 1983), pp. 184–189.

*Primary Examiner*—Sidney Marantz
*Attorney, Agent, or Firm*—Oblon, Fisher, Spivak, McClelland, & Maier

[57] ABSTRACT

Monoclonal anti-human protein C antibodies which bind to the heavy chain of protein C are disclosed.

8 Claims, No Drawings

MONOCLONAL ANTI-PROTEIN C ANTIBODY, ITS PREPARATION AND USE THEREOF

This invention relates to a new monoclonal antibody produced by a hybridoma cell line.

More particularly, it relates to a new monoclonal protein C antibody produced by a hybridoma cell line, to a process for its preparation by a hybridoma cell line, to a hybridoma cell line secreting said antibody, to a process for purifying protein C using said antibody, to a enzyme-linked immunosorbent assay (hereinafter referred to ELISA) of protein C and radioimmunoassay (hereinafter referred to RIA) of protein C.

The monoclonal anti-protein C antibody of this invention can be prepared from cell culture of a mammalian hybridoma cell line produced by fusing a mammalian spleen cell and a mammalian myeloma cell in which the spleen cell is taken from the mammal immunized with protein C originated in a mammal.

Fusion between a spleen cell and a myeloma cell is achieved by bringing them into contact in the presence of a fusion promoter (e.g. polyethyleneglycol). A small percentage of spleen cells and myeloma cells are fused to produce hybridoma. Further, thus obtained hybridomas secrete various antibodies according to a variety of fused spleen cells. But, it is possible to isolate a hybridoma secreting desired antibody from thus obtained hybridomas by cloning.

Thus obtained and cloned hybridoma can be grown in a nutrient medium or in a peritoneal cavity of a mammal, and the produced antibody can be purified from culture supernatant, or ascitic fluid or serum of the mammal in a conventional manner which are generally employed in the isolation and purification of protein from natural or artificial sources. As such a manner, there are exemplified, an isolation and purification method such as centrifugation, dialysis, precipitation with ammonium sulfate, column chromatography using DEAE-cellulose, gel filtration, affinity column chromatography, lyophilization, and the like.

The advantage of this technique is that it provides a source of specific anti-protein C antibody directed against only a certain determinant and uncontaminated by antibodies raised by an antigenic impurities contained in the protein C preparation used. Another advantage of the technique is that substantial quantities of desired anti-protein C antibody may easily be provided.

Thus obtained monoclonal anti-protein C antibody of this invention have a binding ability to protein C, and is adoptable as an immunoadsorbent in an immunoadsorption purification process for protein C. More particularly, a monoclonal anti-protein C antibody of this invention can be bound to polysaccharide by reacting it with an activated polysaccharide (e.g. CNBr-activated Sepharose 4B (made by Pharmacia Fine Chemicals AB) in a conventional manner.

The invention is described by the following experimental details which are given by way of example, not of limitation.

EXAMPLE 1

Preparation of a monoclonal anti-human protein C antibody (i) Preparation of immunized spleen cells Protein C was purified from human plasma, showing single band electrophoretically. Thirty $\mu$g of the protein C solution was administered to each of 6 female BALB/c mice by intraperitoneal injection together with 100 $\mu$l of diphtheria and tetanus toxoids and pertussis vaccine (made by the Institute of Microbiology of Osaka University; $2 \times 10^{10}$ Bordetella pertussis are included in 1 ml). In Experiment 1, 14 days later, additional 30 $\mu$g of the protein C in saline was administered intraperitoneally to each of 3 mice. After 15 days of the second administration, the same amounts of protein C in saline was administered intravenously to the mice. In Experiment 2, 30 $\mu$g of the protein C was administered intraperitoneally to each of the remained 3 mice with the same toxoids and vaccine after 14 days of first administration. After 30 days of second administration, 30 $\mu$g of protein C in saline was administered intravenously to the mice. After 4 days of the last administration, 2 mice in Experiment 1 (1 mouse died) and 3 mice in Experiment 2 were sacrificed, and their spleens were taken to use for the cell fusion.

(ii) Production of hybridoma

The spleen cells prepared by teasing spleens with forceps were fused with mouse myeloma cells P3 X63 Ag8 U1 by the method of Köhler and Milstein (c.f. Nature, 256, 495-497 (1975)). The myeloma cells were provided by Dr. T. Watanabe, Saga Medical School, Saga-ken, Japan.

Namely, the spleen cells were suspended in Dulbecco's modified Eagle's minimum essential medium (hereinafter referred to D-MEM). The erythrocytes in the suspension were destroyed by treating with a mixture of 0.83% ammonium chloride solution (9 volume) and 0.17M tris(hydroxymethyl)aminomethane-hydrochloric acid buffer solution (pH 7.65, 1 volume) at 4° C. for 5 minutes and removed off by centrifugation. The mouse myeloma cells which were cultured in D-MEM supplemented with 15% fetal bovine serum and spleen cells were washed several times with D-MEM.

To the suspension of the mouse myeloma cells ($4 \times 10^7$ cells) was added the suspension of the spleen cells ($2 \times 10^8$ cells). The mixture was well mixed in 50 ml plastic tube (Corning 50 ml centrifuge tube, made by Corning Glass Works). The medium was removed off by centrifugation. The cells were warmed in a water bath to 37° C. To the cells was gradually added 45% polyethyleneglycol (made by Sigma; average molecular weight was 4,000) solution (1 ml) in the course of one minute, while shaking. The mixture was allowed to stand at room temperature for 7 minutes. The cell fusion reaction was stopped by adding 15 ml of D-MEM drop by drop to the reaction mixture in the course of 5 minutes. After a large volume of D-MEM was added to the mixture, the mixture was centrifuged to remove supernatant. To the residue was added complete medium comprising D-MEM supplemented with 15% fetal bovine serum (made by Centaurus, Lot 757), 2 mM glutamine, $2 \times 10^{-5}$M 2-mercaptoethanol, 100 $\mu$g/ml streptomycin sulfate, 100 U/ml penicillin G, 80 $\mu$g/ml gentamicin sulfate and 0.25 $\mu$g/ml Fungizone (Amphotericin B, GIBCO Lab.) (hereinafter referred to CM). After the mixture was slightly mixed, 1 ml of the resultant fused cell suspensions was distributed in each well of ten 24-well plates (Nunc) at a ratio of $1 \times 10^6$ spleen cells per well. One day after the incubation at 37° C. in 5% carbon dioxide atmosphere, 1 ml of CM containing aminopterine ($4 \times 10^{-7}$M), thymidine ($1.6 \times 10^{-5}$M) and hypoxanthine ($1 \times 10^{-4}$M) (HAT medium) was added to each well. After one day, a half volume of the medium in each well was removed by suction and that HAT medium was added to each well every second or third day.

Fourteen days after the cell fusion, growth of hybrid cells was observed in almost all wells.

(iii) Assay of anti-protein C antibody

To each well of 96-well plates (made by Cooke, M-174, cup U rigid immulon) was added 100 μl of 50 μg/ml protein C solution or bovine serum albumin solution, and the plates were incubated at 4° C. overnight for the well to be coated with protein C. Then, a solution of bovine serum albumin (20 μl/ml) was added to block well completely. To each well 100 μl of the above-obtained supernatant of the hybridoma culture was added and was incubated at 37° C. for 90 minutes. After washed with phosphate buffered saline (hereinafter referred to PBS) 3 times, 100 l of affinity chromatography-purified, $^{125}I$-labelled goat anti-mouse IgG F(ab')$_2$ solution (10,000 cpm, specific activity 1 Ci/μg IgG) was added thereto and was incubated at 37° C. 1 hour. The radioactivity of each well was determined by a gamma scintillation counter. Cultures showing binding activity to protein C, not to bovine serum albumin, were selected as culture producing anti-human protein C antibody. Anti-protein C activity was detected in 1 culture of 29 cultures assayed in Experiment 1 and 51 cultures of 226 cultures assayed in Experiment 2.

(iv) Cloning of a hybridoma producing anti-human protein C antibody

Twenty hybridoma cell cultures which showed high binding activity to protein C were cloned by limiting dilution in 96-well flat-bottomed micro test plate (made by NUNC) using BALB/c mouse thymocytes as feeder layer ($5 \times 10^6$ cells/ml).

(v) Purification of monoclonal anti-human protein C antibody

The above-obtained hybridoma was transplanted intraperitoneally to a BALB/c mouse which had been adminstered with tetramethylpentadecane 1 week earlier. After about 1 week, ascites was taken from peritoneal cavity of the mouse, from which monoclonal anti-protein C antibody was isolated by 50% saturated ammononium sulfate solution.

Namely, after removing hybridoma cells from the ascitic fluid by centrifugation, to the supernatant was gradually added ammonium sulfate at a final concentration of 50% saturation while stirring. The mixture was stirred under ice-cooling for 30 minutes and allowed to stand for 60 minutes. After centrifuging the mixture, resultant residue was dissolved in a small volume of 20 mM tris(hydroxymethyl)aminoethane-hydrochloric acid-20 mM NaCl buffer (pH 7.9), was dialyzed against the same buffer and was subjected to a column chromatography on DEAE-cellulose (DE52, made by Whatman Chemical Separation Ltd.) equilibrated with the same buffer. Elution of the monoclonal antibody was carried out with a linear gradient of 20 mM tris(hydroxymethyl)aminomethane-hydrochloric acid-20 mM NaCl buffer (pH 7.9) and 40 mM tris(hydroxymethyl)aminomethane-hydrochloric acid-0.5M NaCl buffer (pH 7.9). Thus obtained eluate was used as an immunoadsorbent in a purification process for protein C, particulars of which are described in Example 2 (ii), and as antibodies of ELISA for human protein C, particulars of which are described in Example 2 (iii).

(vi) Measurement of molecular weight of antibody:

Molecular weight of antibody was determined by SDS-polyacrylamide gel electrophoresis.

(1) Under non-reducing condition:

(a) Monoclonal anti-human protein C antibody 1-18-10 produced by Mouse hybridoma PC 1-18-10:
194,000

(b) Monoclonal anti-human protein C antibody 3-15-7 produced by Mouse hybridoma PC 3-15-7:
202,000

(c) Monoclonal anti-human protein C antibody 2-41-3 produced by Mouse hybridoma PC 2-41-3:
192,000

(d) Monoclonal anti-human protein C antibody 2-105-6 produced by Mouse hybridoma PC 2-105-6:
192,000

(e) Monoclonal anti-human protein C antibody 3-54-5 produced by Mouse hybridoma PC 3-54-5:
185,000

(2) Under reduced condition:

Monoclonal anti-human protein C antibody thus obtained was reduced by 2-mercaptoethanol. In this condition monoclonal anti-human protein C antibody was dissociated to 2 molecules.

(a) Monoclonal anti-human protein C antibody 1-18-10 produced by Mouse hybridoma PC 1-18-10:
26,000 and 45,000

(b) Monoclonal anti-human protein C antibody 3-15-7 produced by Mouse hybridoma PC 3-15-7:
29,000 and 46,000

(c) Monoclonal anti-human protein C antibody 2-41-3 produced by Mouse hybridoma PC 2-41-3:
27,000 and 50,000

(d) Monoclonal anti-human protein C antibody 2-105-6 produced by Mouse hybridoma PC 2-105-6:
26,000 and 46,000

(e) Monoclonal anti-human protein C antibody 3-54-5 produced by Mouse hybridoma PC 3-54-5:
28,000 and 46,000

(vii) Identification of immunoglobulin class of an antibody

Culture supernatant were added with equal volume of saturated ammonium sulfate solution and allowed to stand for 1 hour on ice. The precipitates obtained by centrifugation were dissolved in one tenth volume of PBS.

Identification of immunoglobulin of antibodies thus obtained was conducted by the method of Ouchterlony's double immunodiffusion method. Polyclonal goat antibodies (made by Miles) were used to characterize each subclass of monoclonal antibodies.

Thus obtained monoclonal anti-protein C antibodies are as follows.

(1) Monoclonal anti-human protein C antibody 1-18-10 produced by Mouse hybridoma PC 1-18-10:
(a) Subclass: $IgG_1$ (2) Monoclonal anti-human protein C antibody 2-22-1 produced by Mouse hybridoma PC 2-22-1:
(a) Subclass: $IgG_1$ (3) Monoclonal anti-human protein C antibody 2-27-4 produced by Mouse hybridoma PC 2-27-4:
(a) Subclass: $IgG_{2a}$ (4) Monoclonal anti-human protein C antibody 2-41-3 produced by Mouse hybridoma PC 2-41-3:
  (a) Subclass: IgG$_{2b}$
(5) Monoclonal anti-human protein C antibody 2-45-9 produced by Mouse hybridoma PC 2-45-9:
  (a) Subclass: IgG$_1$
(6) Monoclonal anti-human protein C antibody 2-47-8 produced by Mouse hybridoma PC 2-47-8:
  (a) Subclass: IgG$_1$
(7) Monoclonal anti-human protein C antibody 2-95-2 produced by Mouse hybridoma PC 2-95-2:
  (a) Subclass: IgG$_1$
(8) Monoclonal anti-human protein C antibody 2-97-10 produced by Mouse hybridoma PC 2-97-10:
  (a) Subclass: IgG$_1$
(9) Monoclonal anti-human protein C antibody 2-101-17 by Mouse hybridoma PC 2-101-17
  (a) Subclass: IgG$_1$
(10) Monoclonal anti-human protein C antibody 2-105-6 produced by Mouse hybridoma PC 2-105-6:
  (a) Subclass: IgG$_1$
(11) Monoclonal anti-human protein C antibody 2-115-1 produced by Mouse hybridoma PC 2-115-1:
  (a) Subclass: IgG$_1$
(12) Monoclonal anti-human protein C antibody 3-15-7 produced by Mouse hybridoma PC 3-15-7:
  (a) Subclass: IgG$_1$
(13) Monoclonal anti-human protein C antibody 3-54-5 produced by Mouse hybridoma PC 3-54-5:
  (a) Subclass: IgG$_{2a}$

EXAMPLE 2

Application of a monoclonal anti-human protein C antibody to a process for the purification of protein C (i) Coupling of a monoclonal anti-protein C antibody to CNBr-activated Sepharose 4B (made by Pharmacia Fine Chemicals AB)

CNBr-activated Sepharose 4B (0.7 g) was washed with 1 mM hydrogen chloride and coupling buffer containing 0.1M sodium bicarbonate (pH 8.3) and 0.5M sodium chloride, successively, to prepare a solution of CNBr-activated Sephrose 4B in coupling buffer (3 ml). To 1 ml of the solution was added 3 ml of coupling buffer solution of monoclonal anti-human protein C antibody 3-15-7 (3.7 mg, protein) prepared in Example 1, which had been prepared by dialysis. The resultant mixture was allowed to shake at room temperature for 2 hours. After washing the mixture by 5 to 7 ml of PBS on G3 glass filter, 1M ethanolamine-HCl (4 ml, pH 8.0) was added thereto and was allowed to shake at a room temperature for 2 hours to block remaining active site. After blocking, the resultant antibody-coupled Sepharose 4B solution was washed with a solution of 0.1M acetate buffer (pH 4.0) containing 0.5M sodium chloride and coupling buffer mentioned above, successively (three times) and was equilibrated with 25 mM sodium phosphate buffer (pH 7.4) containing 0.5 sodium chloride after washing 20 ml of PBS containing 0.1% bovine serum albumin. Thus obtained CNBr-activated Sepharose 4B coupled monoclonal anti-protein C antibody (hereinafter referred to antibody-coupled Sepharose 4B, specifically Column 3-15-7, was used for affinity column chromatography.

(ii) Adsorption and elution of protein C to antibody-coupled Sepharose 4B

Antibody-coupled Sepharose 4B (0.5 ml) was packed to a column which was equilibrated with 25 mM sodium phosphate buffer (pH 7.4) containing 0.5M sodium chloride. Crude human protein C applied for affinity chromatography was prepared as followed. To 25 ml of human plasma from blood of 5 healthy men was added 2 ml of 1M BaCl$_2$ in the presence of benzamidine. Precipitate was collected by centrifugation, following washing with 0.15M sodium chloride solution containing 5 mM benzamidine. The precipitate is dissolved in 0.25M EDTA and 5 mM benzamidine solution. The protein solution obtained by centrifugation is dialyzed against PBS. The solution containing crude human protein C was loaded on the column, washed with PBS, eluted with 3M potassium thiocyanate solution. Protein C was assayed by ELISA described later. Protein C activity was not detected in passed-through fractions from column, so almost all parts of protein C was thought to have bound to the column. Yields of protein C eluted was 73.1% of the charged protein C, on the other hand, only 1% of protein C and a large amounts of contaminated protein passed through.

The results are shown in the following Table 1.

TABLE 1

| Affinity chromatography of crude protein C using Column 3-15-7 | | | | |
|---|---|---|---|---|
| | Protein µg | Protein C µg | Yield % | Purification factor, fold |
| Charged crude protein C solution | 804 | 6.24 | 100 | 1.0 |
| passed-through fraction | 781 | 0.064 | 1 | 0.0 |
| 3M KSCN eluate | 48.5 | 4.56 | 73.1 | 12.1 |

(iii) Enzyme-linked immunosorbent assay for human protein C using anti-human protein C monoclonal antibody:

Anti-human protein C monoclonal antibody was purified as described above. Conjugation of horse radish peroxidase (hereinafter referred to POD) (type IV, made by Sigma) to monoclonal antibody was performed as described by Nakane and Kawaoi (Nakane, P. K. and A. Kawaoi, J. Histochem. Cytochem. 22, 1084(1974)). One step sandwich ELISA was performed as follows. One hundred µl of POD-conjugated anti-human protein C monoclonal antibody (A) in PBS containing 0.5% bovine serum albumin and 0.05% Tween 20 (polyoxyethylene sorbitan monolaurate, made by Kao Atlas Co., Ltd.) and 100 µl of sample or purified protein C (standard) were added to each well of 96-well plate (made by Sumitomo Bakelite) precoated with 10 µg/ml of anti-human protein C monoclonal antibody (B) at room temperature for 1 hour, followed by washing three times with PBS containing 0.1% bovine serum albumin and 0.05% Tween 20. After incubation at room temperature for 1 hour, the wells were washed in the same manner, then 200 µl of substrate solution (2.5 mg/ml O-phenylenediamine dihydrochloride and 0.018% H$_2$O$_2$ in 0.1M citrate-phosphate buffer, pH 5.4) was added. After 30 minutes the reaction was stopped by the addition of 50 µl of 20% sulfonic acid. The absorbance was read on a MR miro-ELISA microreader (made by Dynatech Inc.) at wavelength of 490 nm.

The results are shown in the following Table 2.

TABLE 2

Combination of monoclonal antibodies applicable for ELISA of human protein C

|  |  | (A): enzyme-conjugated monoclonal antibody | | | |
|---|---|---|---|---|---|
|  |  | 2-101-17 | 2-105-6 | 3-15-7 | 3-54-5 |
| (B) Monoclonal antibody for coating | 1-18-10 | 1 | 1 | 1 | 3 |
|  | 2-41-3 | 2 | 1 | 2 | 1 |
|  | 2-27-4 | 2 | 1 | 2 | 1 |
|  | 2-101-17 | 3 | 1 | 3 | 1 |
|  | 2-115-1 | 3 | 1 | 3 | 1 |
|  | 2-47-8 | 3 | 1 | 3 | 1 |
|  | 2-45-9 | 1 | 1 | 1 | 1 |
|  | 2-105-6 | 1 | 3 | 1 | 1 |
|  | 3-15-7 | 3 | 1 | 3 | 1 |
|  | 3-54-5 | 1 | 1 | 1 | 3 |

1: applicable
2: poorly applicable
3: not applicable

This results show that the use of same antibody for enzyme-conjugation and coating is impossible because of the competition on the certain determinant. This means that applicable combination of antibodies comprise antibodies directed to different determinant. These antibodies are classified as follows.

Group A: 1-18-10, 3-54-5
Group B: 2-105-6
Group C: 3-15-7, 2-101-17, 2-115-1, 2-47-8
Group D: 2-27-4, 2-41-3
Group E: 2-45-9

Combination of monoclonal antibodies for best sensitive assay is 2-105-6 for coating and 3-54-5 for enzyme-conjugation. ELISA with this combination was able to detect 1–100 ng/ml of purified protein C.

Further, ELISA with this combination was possible to detect protein C in human plasma after dilution of 80 to 2,560 fold. The concentration of protein C in human plasma determined in this ELISA was 4.96 μg/ml.

(iv) Inhibition of activated protein C activity by monoclonal antibody

Protein C is activated by thrombin to protein Ca which acts as a serine protease to activated Factor V or synthetic substrate. Protein C activated by the reaction with thrombin-coupled Sepharose 4B at 37° C. for 1 hour was incubated with 100 μg/ml of monoclonal antibody at 37° C. overnight. After the incubation, synthetic fluorescent substrate (t-butyloxycarboxy-Leu-Ser-Thr-Arg-4-methylcoumaryl-7-amide) was added to the incubation mixture and the mixture was incubated at room temperature for 30 minutes. The measurements of fluorescence emitted by hydrolytic activity of protein Ca was carried out with excitation at 380 nm and emission at 460 nm.

Antibodies 1-18-10 and 3-54-5 inhibited the protein Ca activity at the ratio of 78.7% and 79.4%. Antibodies 2-27-4, 2-41-3, 2-45-9, 2-47-8, 2-101-17, 2-105-6 and 2-115-1 showed no inhibition.

(v) Inhibition of the effect of activated protein C to Factor Va by monoclonal antibody The effect of monoclonal antibody to the inactivation of Factor Va (activated Factor V) by protein C was examined by measuring the change in prothrombinase activity of Factor Va using fluorescent synthetic substrate (t-butyloxycarboxy-Val-Pro-Arg-4-methylcoumaryl-7-amide) in the presence of activated Factor X, Calcium ion and phospholipid.

Antibody 3-54-5, 1-18-10, 2-101-17, 2-105-6 and 2-115-1 inhibited the inactivation of Factor Va by protein C.

(vi) Inhibition of the activation of protein C by monoclonal antibody

Protein C was incubated with 500 μg/ml of monoclonal antibody at 37° C. overnight, then thrombin-coupled Sepharose 4B was added and the mixture was incubated at 37° C. for 1 hour with shaking. After centrifugation of the mixture, fluorescent synthetic substrate as described above was added to the supernatant and the mixture was incubated at room temperature for 30 minutes. The measurement of fluorescence was carried out in the same manner.

Antibody 2-45-9, 1-18-10 and 3-54-5 inhibited the reaction. From the results of example 2 (iv) and this example, antibody 2-45-9 was thought to inhibit the effect of thrombin to the heavy chain of protein C.

(vii) Blocking of the inhibitory effect of protein C inhibitor on protein Ca by monoclonal antibody 30 μl of protein Ca (2.0 μg) and 20 μl of monoclonal antibody (9.6 μg) were incubated in 750 μl of the buffer consisting of 0.05M Tris-HCl, pH 7.5, 0.1M NaCl and 0.1% bovine serum albumin at 4° C. overnight. Then, 200 μl of protein C inhibitor (2.0 μg) was added, and residual activity of protein Ca was measured using the synthetic fluorescent substrate (t-butyloxycarboxy-Leu-Ser-Thr-Arg-4-methylcoumaryl-7-amide). When the protein Ca was treated with antibody 1-18-10, a half of the enzyme activity remained before addition of the inhibitor, however, this activity decreased very little even 50 minutes after addition of the inhibitor. Antibody 1-18-10 was thought to block the action of the protein C inhibitor on protein Ca.

(viii) Inhibition of the stimulatory effect of protein S on the protein Ca-catalyzed inactivation of coagulation factor Factor Va The protein Ca-catalyzed inactivation of coagulation Factor Va is stimulated about fifteen times by another vitamin K-dependent protein S. Protein Ca was treated beforehand with the monoclonal antibody at 4° C. overnight. When the effect of protein Ca on the inactivation of Factor Va was examined by measuring the change in prothrombinase activity of Factor Va as described in Example 2 (v), the stimulatory effect of protein S on the action of protein Ca was specifically inhibited 90% by antibody 2-115-1 and 60% by 2-101-17.

(ix) Antigenic determinant of monoclonal antibody

Antigenic determinant of monoclonal antibody on protein C was examined with immunoblotting system (Bio-Rad Lab.) using goat anti-mouse IgG as second antibody and autoradiography.

Antibody 1-18-10, 2-45-9, 2-105-6, 3-15-7 and 3-54-5 were found to bind to the heavy chain of protein C. Antibody 2-27-4, 2-41-3 2-95-2 and 2-115-1 were assumed to bind to the light chain. Antibody 2-47-8 and 2-97-10 were speculated to direct toward. The antigenic determinant containing amino acids on both the light and heavy chains of protein C or toward a specific conformation of intact protein C.

What we claim is:

1. A monoclonal anti-human protein C antibody, wherein said antibody has the following characteristics:
   (i) molecular weight determined by SDS-polyacrylamide gel electrophoresis:
      ca. 192,000
   (ii) molecular weight of reduced products by 2-mercaptoethanol:

ca. 26,000 and 46,000
(iii) subclass:
IgG$_1$
(iv) inhibitory activity toward protein Ca activity:
negative
(v) inhibitory activity toward Factor Va:
positive, and
(vi) antigenic determinant:
binds to the heavy chain of protein C.

2. A monoclonal anti-human protein C antibody of claim 1, wherein said antibody is produced by a hybridoma deposited at the NCACC under accession number 86090302.

3. A monoclonal anti-human protein C antibody, wherein said antibody has the following characteristics:
(i) molecular weight determined by SDS-polyacrylamide gel electrophoresis:
ca. 185,000
(ii) molecular weight of reduced products by 2-mercaptoethanol:
ca. 28,000 and 46,000
(iii) subclass:
IgG$_{2a}$
(iv) inhibitory activity toward protein Ca activity:
positive
(v) inhibitory activity toward Factor Va:
positive, and
(vi) antigenic determinant:
binds to the heavy chain of protein C.

4. A monoclonal anti-human protein C antibody of claim 3, wherein said antibody is produced by a hybridoma deposited at the NCACC under accession number 86090303.

5. The hybridoma cell line deposited at the NCACC under accession number 86090302.

6. The hybridoma cell line deposited at the NCACC under accession number 86090303.

7. An enzyme-linked immunosorbant assay method for the measurement of protein C, which comprises conducting an ELISA using a first monoclonal antibody which recognizes protein C, wherein said first antibody is coated on a surface, and using a second monoclonal antibody which recognizes protein C, wherein said second antibody is conjugated with a detectable enzyme,
said first antibody having the following characteristics:
(i) molecular weight determined by SDS-polyacrylamide gel electrophoresis:
ca. 192,000
(ii) molecular weight of reduced products by 2-mercaptoethanol:
ca. 26,000 and 46,000
(iii) subclass:
IgG$_1$
(iv) inhibitory activity toward protein Ca activity:
negative
(v) inhibitory activity toward Factor Va:
positive, and
(vi) antigenic determinant:
binds to the heavy chain of protein C;
and
said second antibody having the following characteristics:
(i) molecular weight determined by SDS-polyacrylamide gel electrophoresis:
ca. 185,000
(ii) molecular weight of reduced products by 2-mercaptoethanol:
ca. 28,000 and 46,000
(iii) subclass:
IgG$_{2a}$
(iv) inhibitory activity toward protein Ca activity:
positive
(v) inhibitory activity toward Factor Va:
positive, and
(vi) antigenic determinant:
binds to the heavy chain of protein C.

8. The method of claim 7 wherein said first antibody is produced by a hybridoma deposited at the NCACC under accession number 86090302 and said second antibody is produced by a hybridoma deposited at the NCACC under accession number 86090303.

* * * * *